United States Patent
Carbonne Dit Leychert Garenne et al.

(10) Patent No.: US 11,166,683 B2
(45) Date of Patent: Nov. 9, 2021

(54) SPECTRAL PILEUP CORRECTION FOR PHOTON-COUNTING X-RAY DETECTORS

(71) Applicant: Prismatic Sensors AB, Stockholm (SE)

(72) Inventors: Louis Carbonne Dit Leychert Garenne, Stockholm (SE); Fredrik Grönberg, Stockholm (SE); Erik Fredenberg, Stockholm (SE)

(73) Assignee: PRISMATIC SENSORS AB, Stockholm (SE)

( * ) Notice: Subject to any disclaimer, the term of this patent is extended or adjusted under 35 U.S.C. 154(b) by 0 days.

(21) Appl. No.: 16/806,486

(22) Filed: Mar. 2, 2020

(65) Prior Publication Data
US 2021/0267562 A1 Sep. 2, 2021

(51) Int. Cl.
*A61B 6/00* (2006.01)
*A61B 6/03* (2006.01)

(52) U.S. Cl.
CPC ............ *A61B 6/4241* (2013.01); *A61B 6/032* (2013.01); *A61B 6/502* (2013.01); *A61B 6/5258* (2013.01)

(58) Field of Classification Search
CPC ..... A61B 6/4241; A61B 6/032; A61B 6/5205; A61B 6/482; A61B 6/5258; A61B 6/502; G01T 1/171
See application file for complete search history.

(56) References Cited

U.S. PATENT DOCUMENTS

| | | |
|---|---|---|
| 2012/0112088 A1 | 5/2012 | Abraham |
| 2015/0182176 A1 | 7/2015 | Jin et al. |
| 2015/0327827 A1 | 11/2015 | Teshigawara |
| 2016/0076935 A1 | 3/2016 | Daerr et al. |
| 2016/0195623 A1 | 7/2016 | Wang et al. |
| 2017/0231584 A1 | 8/2017 | Konno |
| 2019/0313993 A1* | 10/2019 | Zhou ..................... A61B 6/502 |

OTHER PUBLICATIONS

Knoll, "Radiation Detection and Measurement," 3rd edition, John Wiley & Sons, 2000, pp. 119-122.

(Continued)

*Primary Examiner* — Courtney D Thomas
(74) *Attorney, Agent, or Firm* — Nixon & Vanderhye

(57) ABSTRACT

Disclosed is a method and corresponding system for correcting the pileup effect in energy-discriminating photon-counting detectors. According to a first aspect, there is provided a method for pileup correction in a non-paralyzable energy-discriminating photon-counting x-ray detector operating based on a number of energy bins. The method includes adding, for each of a number of energy bins, a correction term to the detected signal of the energy bin, the correction term being a product of two separable parameterized functions, each of which includes at least one parameter, where a first parameterized function depends on a weighted sum of the detected signal over the energy bins, and where a second parameterized function depends on the detected signal(s) in one or several energy bin(s). By assuming separability and ignoring any cross correlations, the number of parameters and the complexity of the pileup correction algorithm are reduced substantially.

21 Claims, 13 Drawing Sheets

(56) References Cited

OTHER PUBLICATIONS

Grönberg et al., "Count statistics of nonparalyzable photon-counting detectors with nonzero pulse length," Med Phys., 2018, vol. 45, No. 8, pp. 3800-3811.
Sabbatucci et al., "First principles pulse pile-up balance equation and fast deterministic solution," Radiation Physics and Chemistry, 2017, vol. 137, pp. 12-17.
Cammin et al., "Evaluation of models of spectral distortions in photon-counting detectors for computed tomography," Journal of Medical Imaging, 2016, vol. 3, No. 2, 13 pages.
Feng et al., "Neural-networks-based Photon-Counting Data Correction: Pulse Pileup Effect," IEEE, 2018, pp. 1-14.
Alvarez, "Near optimal neural network estimator for spectral x-ray photon counting data with pileup," ArXiv, 2017, pp. 1-11.
Alvarez et al., "Energy-selective Reconstructions in X-ray Computerized Tomography," Phys. Med. Biol., 1976, vol. 21, No. 5, pp. 733-744.
International Search Report, dated Aug. 11, 2020, from corresponding PCT Application No. PCT/SE2020/050230.

\* cited by examiner

SPECTRAL PILEUP CORRECTION FOR PHOTON-COUNTING X-RAY DETECTORS

The project leading to this application has received funding from the European Union's Horizon 2020 research and innovation programme under grant agreement No 830294.

TECHNICAL FIELD

The proposed technology relates to x-ray imaging and x-ray detectors, and more particularly to a method and corresponding system for correction of pulse pileup in a photon-counting x-ray detector, and an x-ray imaging system as well as a corresponding computer program and computer-program product.

BACKGROUND

Radiographic imaging such as x-ray imaging has been used for years in medical applications and for non-destructive testing.

Normally, an x-ray imaging system includes an x-ray source and an x-ray detector system. The x-ray source emits x-rays, which pass through a subject or object to be imaged and are then registered by the x-ray detector system. Since some materials absorb a larger fraction of the x-rays than others, an image is formed of the subject or object.

Photon-counting x-ray detectors have emerged as a feasible alternative in some applications. Such photon-counting x-ray detectors have an advantage since in principle the energy for each x-ray photon can be measured, which yields additional information about the composition of the object. This information can be used to increase the image quality and/or to decrease the radiation dose.

However, so-called pulse pileup occurs in photon-counting x-ray detectors when more than one photon hits the detector within the time window that is set by the pulse width in the electronics (the so-called dead time). Pileup leads to a loss of counts because two or more photons end up generating just a single pulse. Pileup also leads to spectral distortion because pulses within a dead time will add to a larger pulse height, which is interpreted as one photon with higher energy, and the pulses will also add to a wider pulse with a tail that may be detected as a second low-energy pulse, or in turn may pileup with subsequent pulses. The effects of pileup on a radiological image include:

- Reduced contrast-to-noise ratio because the increased loss of counts at higher count rates reduces the contrast between areas with different count rates, such as a radiological target.
- Bias in a material-decomposed image because the spectral response of the detector varies with count rate and will be different from the calibrated spectral response if the x-ray tube current is different than at calibration.
- Reduced efficiency of standard x-ray imaging correction processes, such as scatter correction, and data reduction operations, such as binning of pixels or depth segments, because these processes and operations typically assume a linear detector response.

It is therefore desirable to apply a procedure to correct for the deterministic parts of the pileup effect. It is also clear that the pileup correction procedure needs to be applied early in the image chain of an x-ray imaging system, before any other correction process (e.g. scatter correction) or data reduction operation (e.g. binning of detector pixels or depth segments).

The pileup response by photon-counting detectors can be principally divided into two categories: paralyzable and non-paralyzable behavior.[1]

Paralyzable detectors have a dead time that is reset for every new event, which results in an infinitely long dead time if the incident rate is high enough. Consequently, a maximum detected count rate is reached for some incident rate, after which the detected count rates starts to decrease. The detected count rate as a function of incident rate is hence not an injective and invertible function and it is challenging to correct for lost counts.

Non-paralyzable detectors, on the other hand, have a non-extendable (or semi-extendable) dead time, which results in a monotonically increasing (and generally invertible) detected count rate as a function of incident count rate. The detected count rate will reach a plateau at a maximum count rate determined by the reciprocal of the dead time.

For non-paralyzable photon-counting detectors without energy discrimination, well-established models are available that describe the loss of counts due to pileup with high accuracy.[1,2] These models can be inverted and allow for correction of the lost counts.

For photon-counting detectors with energy discrimination, it is necessary to compensate also for spectral distortion, i.e. migration of counts between the energy bins. The correction problem then becomes even more complex, in particular because the bin response function is not, in general, an injective function of the true bin count rate even for non-paralyzable detectors. For low-energy bins, counts may be lost to higher energy bins faster than the increase in bin count rate, which results in a maximum count rate and a drop towards higher rates. This behavior makes it challenging to determine the inverse as there is no one-to-one mapping between detected and true count rate.

One approach for so-called spectral pileup correction is to model the pileup process analytically.[3,4] The model can be inverted, analytically or iteratively, to correct for the effects of pileup. One drawback of this approach is that more or less detailed system knowledge is required (incident spectrum, pulse shape etc.), which is not always available. Another approach is to use data-driven methods based on neural networks or machine learning,[5,6] which do not require any high level of system knowledge.

However, common to all approaches in the prior art is a high level of complexity, either in the algorithm itself as is the case for the analytical methods, or in the number of parameters, as is the case for the data-driven methods. This is generally not a problem if the methods are implemented offline, in a limited scale, or without time or memory constraints. However, for a medical imaging system in a realistic clinical environment the amount of data is large, and time is clearly an issue. Further, if the algorithm is to be located early in the imaging chain before other correction algorithms and data reduction operations, firmware implementation on e.g. an FPGA may be necessary, which adds strong constraints on the number of operations and the number of parameters that the algorithm can make use of. The methods available in the prior art are therefore clearly suboptimal for practical use in medical imaging systems.

SUMMARY

It is a general object to provide improvements related to photon-counting x-ray detectors.

In particular, it is desirable to correct for the pileup effect in such x-ray detectors. Correcting for pileup improves linearity and the spectral response of the detector.

It is a particular object to provide a method for pileup correction in a non-paralyzable energy-discriminating photon-counting x-ray detector.

Another object is to provide a system for pileup correction in a non-paralyzable energy-discriminating photon-counting x-ray detector.

Yet another object is to provide a system for x-ray imaging comprising such a system for pileup correction.

It is also an object to provide a computer-program comprising instructions, which when executed by a processor, cause the processor to perform a method for pileup correction.

Still another object is to provide a computer-program product comprising a non-transitory computer-readable medium having such a computer program stored thereon.

It is a specific object to provide a method for spectral pileup correction that is low in complexity and can be implemented early in the imaging chain, possibly directly in the detector firmware to improve speed and data handling performance of the x-ray imaging system.

These and other objects may be met by at least one of the embodiments described herein.

According to a first aspect, there is provided a method for pileup correction in a non-paralyzable energy-discriminating photon-counting x-ray detector operating based on a number of energy bins. The method comprises adding, for each of a number of energy bins, a correction term to the detected signal of the energy bin, said correction term being a product of two separable parameterized functions, each of which includes at least one parameter, where a first parameterized function depends on a weighted sum of the detected signal over the energy bins, and where a second parameterized function depends on the detected signal(s) in one or several energy bin(s).

According to a second aspect, there is provided a system for pileup correction in a non-paralyzable energy-discriminating photon-counting x-ray detector operating based on a number of energy bins. The system is configured to add, for each of a number of energy bins, a correction term to the detected signal of the energy bin, said term being a product of two separable parameterized functions, each of which includes at least one parameter, where a first parameterized function depends on a sum of the detected signal over the energy bins, and where a second parameterized function depends on the detected signal(s) in one or several energy bin(s).

By way of example, the procedure for pileup correction may thus be split into two separable functions, where the first function depends essentially on the non-spectral signal, and the second function depends essentially on the spectral response, normalized by the non-spectral signal.

By assuming separability and ignoring any cross correlations, the number of parameters and the complexity of the pileup correction algorithm are reduced substantially.

According to a third aspect, there is provided a system for x-ray imaging comprising such a system for pileup correction.

According to a fourth aspect, there is provided a computer-program comprising instructions, which when executed by a processor, cause the processor to perform the method disclosed herein.

According to a fifth aspect, there is provided a computer-program product comprising a non-transitory computer-readable medium having such a computer program stored thereon.

Other advantages will be appreciated when reading the detailed description.

BRIEF DESCRIPTION OF DRAWINGS

The embodiments, together with further objects and advantages thereof, may best be understood by making reference to the following description taken together with the accompanying drawings, in which.

DETAILED DESCRIPTION

Figure 1:
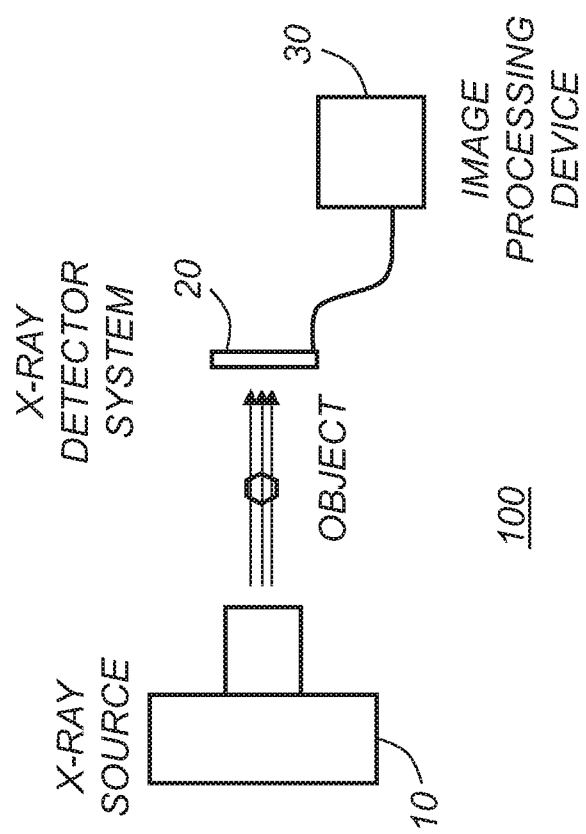
FIG. 1 is a schematic diagram illustrating an example of an overall x-ray imaging system.

It may be useful to begin with a brief overview of an illustrative overall x-ray imaging system, with reference to FIG. 1. In this non-limiting example, the x-ray imaging system 100 basically comprises an x-ray source 10, an x-ray detector system 20 and an associated image processing device 30. In general, the x-ray detector system 20 is configured for registering radiation from the x-ray source 10 that may have passed an object or subject or part thereof. The x-ray detector system 20 is connectable to the image processing device 30 via suitable analog processing and read-out electronics (which may be integrated in the x-ray detector system 20) to enable image processing and/or image reconstruction by the image processing device 30.

Figure 2:
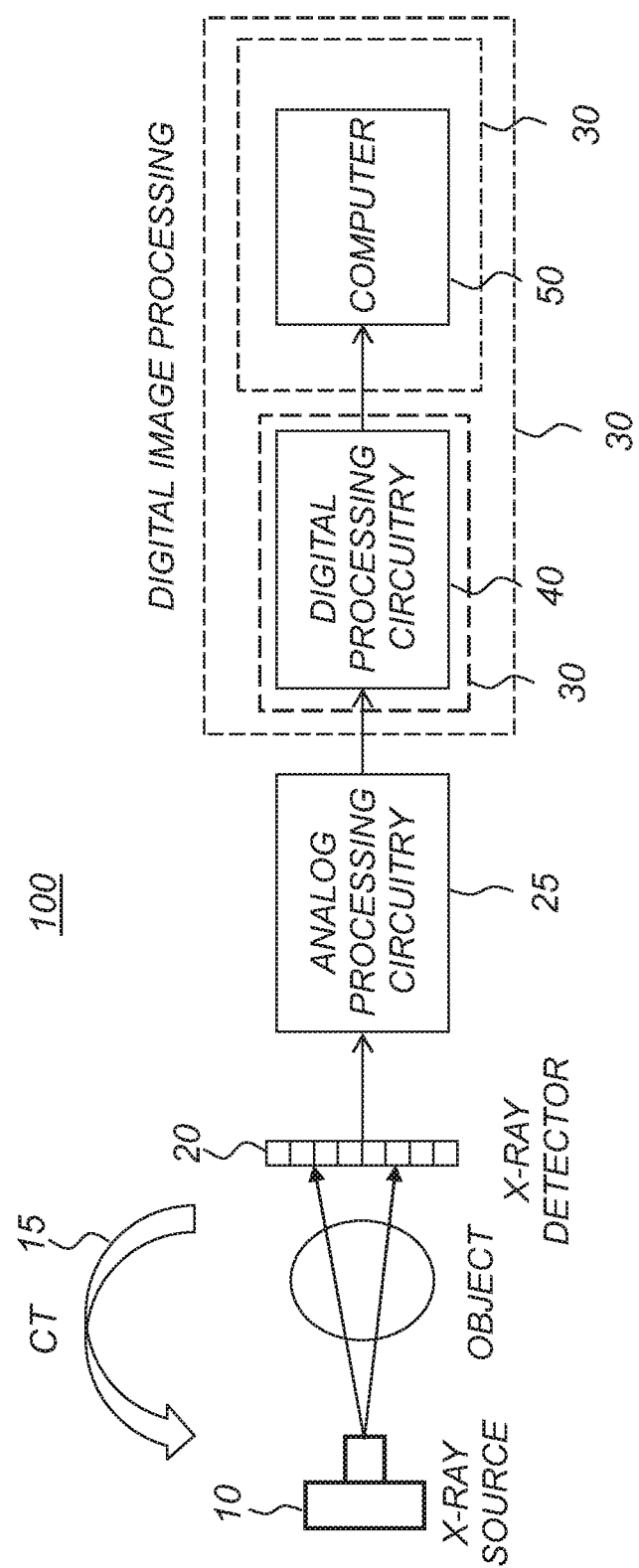
FIG. 2 is a schematic diagram illustrating another example of an x-ray imaging system.

FIG. 2 is a schematic diagram illustrating an example of an x-ray imaging system 100 comprising an x-ray source 10, which emits x-rays; an x-ray detector system 20, which detects the x-rays after they have passed through the object; analog processing circuitry 25, which processes the raw electrical signal from the detector and digitizes it; digital processing circuitry 40, which may carry out further processing operations on the measured data such as applying corrections, storing it temporarily, or filtering; and a computer 50, which stores the processed data and may perform further post-processing and/or image reconstruction.

The overall detector may be regarded as the x-ray detector system 20, or the x-ray detector system 20 combined with the associated analog processing circuitry 25.

The digital part including the digital processing circuitry 40 and/or the computer 50 may be regarded as a digital image processing system 30, which performs image reconstruction based on the image data from the x-ray detector. The image processing system 30 may thus be seen as the computer 50, or alternatively the combined system of the digital processing circuitry 40 and the computer 50, or possibly the digital processing circuitry 40 by itself if the digital processing circuitry is further specialized also for image processing and/or reconstruction.

An example of a commonly used x-ray imaging system is a Computed Tomography (CT) system, which may include an x-ray source that produces a fan or cone beam of x-rays and an opposing x-ray detector system for registering the fraction of x-rays that are transmitted through a patient or object. The x-ray source and detector system are normally mounted in a gantry that rotates around the imaged object.

Accordingly, the x-ray source 10 and the x-ray detector system 20 illustrated in FIG. 1 and FIG. 2 may thus be arranged as part of a CT system, e.g. mountable in a CT gantry.

Figure 3:
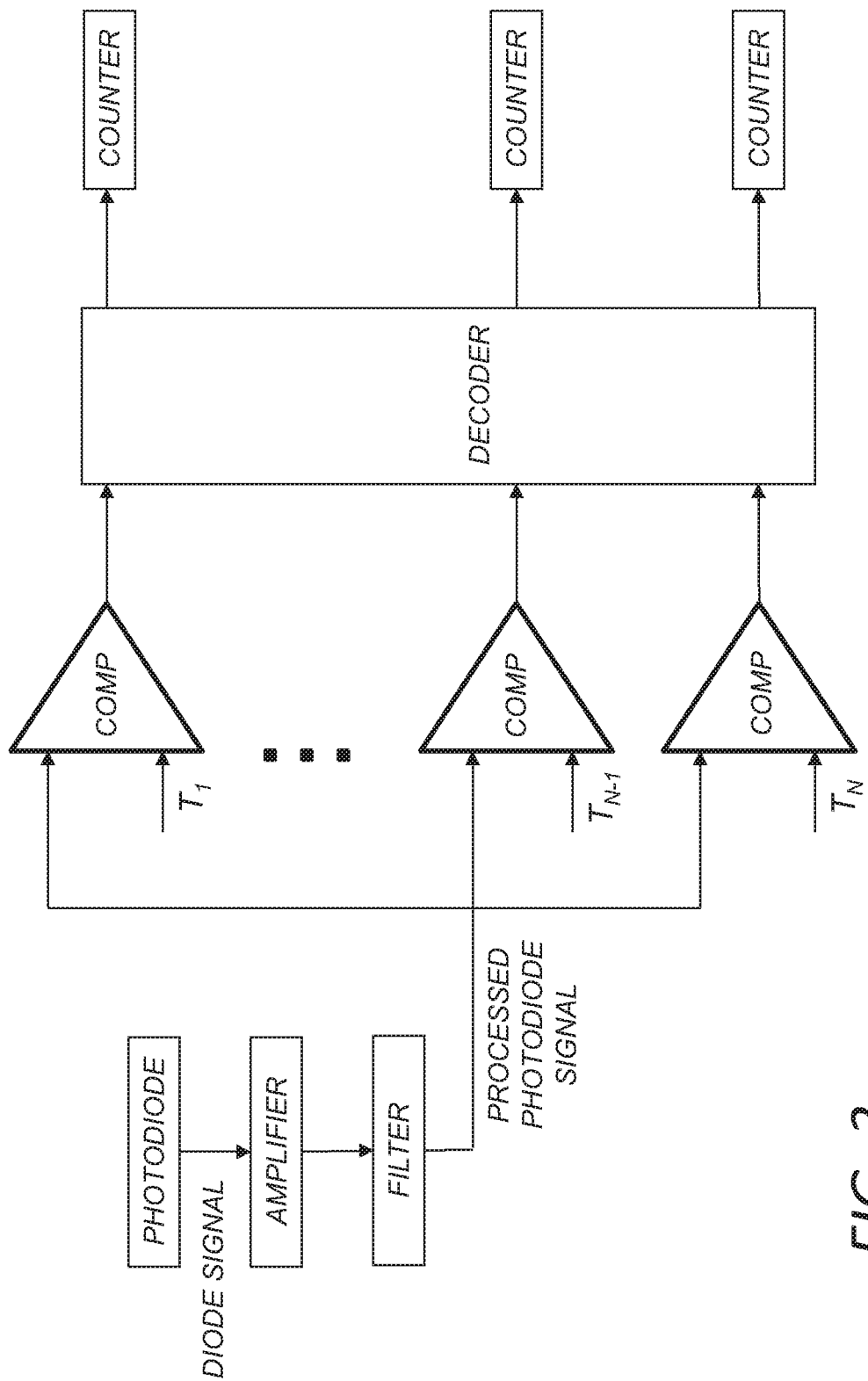
FIG. 3 is a schematic block diagram of a CT system as an illustrative example of an x-ray imaging system.

FIG. 3 is a schematic block diagram of a CT system as an illustrative example of an x-ray imaging system. The CT system comprises a computer 50 receiving commands and scanning parameters from an operator via an operator console 60 that may have a display and some form of operator interface, e.g., keyboard and mouse. The operator-supplied commands and parameters are then used by the computer 50 to provide control signals to an x-ray controller 41, a gantry controller 42 and a table controller 43. To be specific, the x-ray controller 41 provides power and timing signals to the x-ray source 10 to control emission of x-rays onto the object or patient lying on the table 12. The gantry controller 42 controls the rotational speed and position of the gantry 11 comprising the x-ray source 10 and the edge-on photon-counting detector 20. The table controller 43 controls and determines the position of the patient table 12 and the scanning coverage of the patient. There is also a detector controller 44, which is configured for controlling and/or receiving data from the detector 20.

In an embodiment, the computer 50 also performs post-processing and image reconstruction of the image data output from the edge-on photon-counting detector. The computer thereby corresponds to the image processing system 30 as shown in FIGS. 1 and 2. The associated display allows the operator to observe the reconstructed images and other data from the computer.

The x-ray source 10 arranged in the gantry 11 emits x-rays. An x-ray detector 20, e.g. in the form of an edge-on photon-counting detector, detects the x-rays after they have passed through the patient. The edge-on photon-counting detector 20 may for example be formed by a plurality of pixels, also referred to as sensors or detector elements, and the associated processing circuitry, such as ASICs, arranged in detector modules. At least a portion of the analog processing part may be implemented in the pixels, whereas any remaining processing part is implemented in, for instance, the ASICs. In an embodiment, the processing circuitry (ASICs) digitizes the analog signals from the pixels. The processing circuitry (ASICs) may also comprise a digital processing part, which may carry out further processing operations on the measured data, such as applying corrections, storing it temporarily, and/or filtering. During a scan to acquire x-ray projection data, the gantry and the components mounted thereon rotate about an iso-center.

A challenge for x-ray imaging detectors is to extract maximum information from the detected x-rays to provide input to an image of an object or subject where the object or subject is depicted in terms of density, composition and structure. It is still common to use film-screen as detector but most commonly the detectors today provide a digital image.

Modern x-ray detectors normally need to convert the incident x-rays into electrons, this typically takes place through photo absorption or through Compton interaction and the resulting electrons are usually creating secondary visible light until its energy is lost and this light is in turn detected by a photo-sensitive material. There are also detectors, which are based on semiconductors and in this case the electrons created by the x-ray are creating electric charge in terms of electron-hole pairs which are collected through an applied electric field.

Conventional x-ray detectors are energy integrating, the contribution from each detected photon to the detected signal is therefore proportional to its energy, and in conventional CT, measurements are acquired for a single energy distribution. The images produced by a conventional CT system therefore have a certain look, where different tissues and materials show typical values in certain ranges.

There are detectors operating in an integrating mode in the sense that they provide an integrated signal from a multitude of x-rays and the signal is only later digitized to retrieve a best guess of the number of incident x-rays in a pixel.

Figure 4:
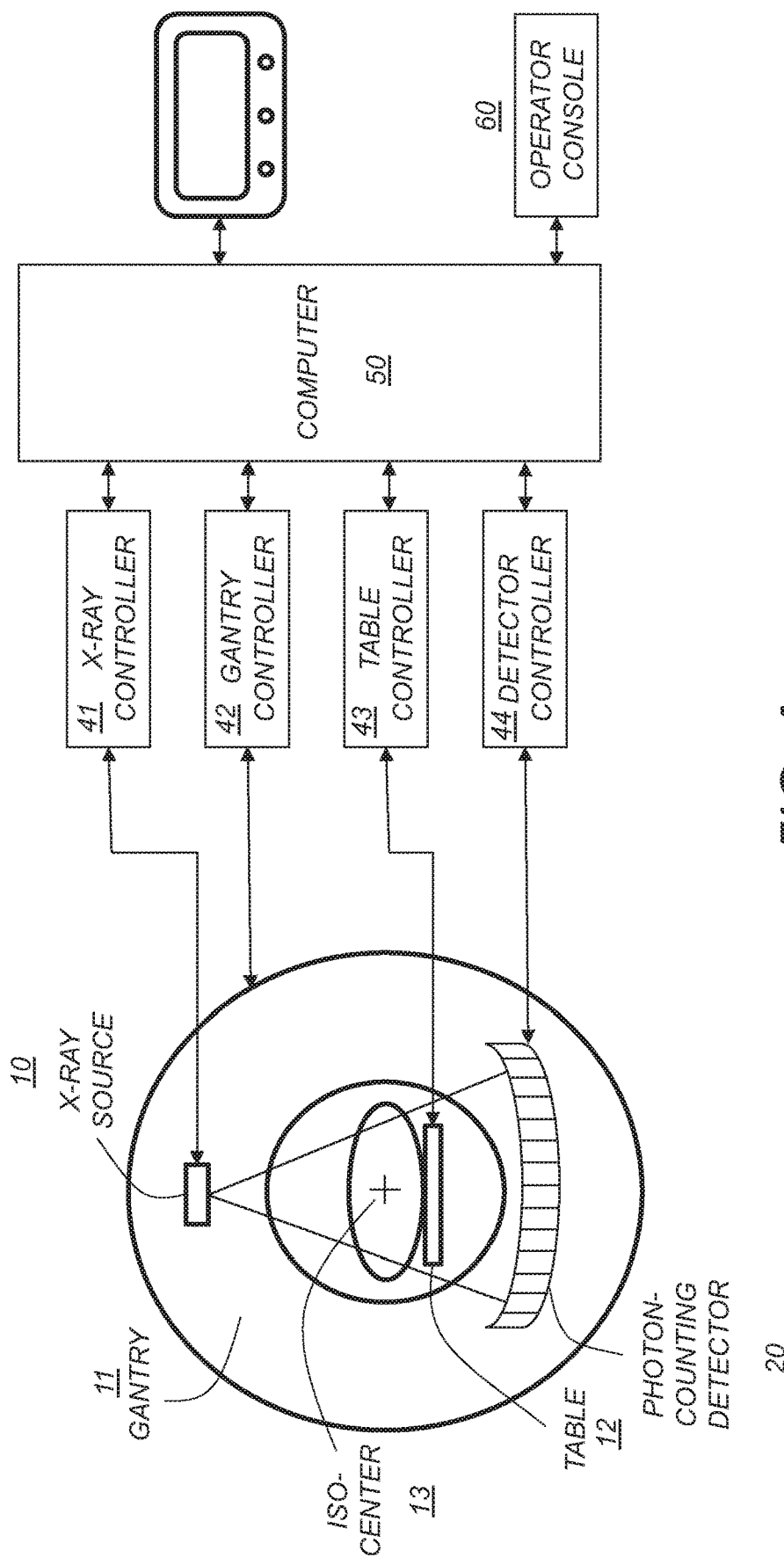
FIG. 4 is a schematic diagram illustrating an example of the conceptual structure for implementing an energy-discriminating photon-counting detector.

However, photon-counting detectors have emerged as a feasible alternative in some applications. The photon-counting detectors have an advantage since in principle the energy for each x-ray photon can be measured, which yields additional information about the composition of the object. Such detectors are referred to as energy-discriminating photon-counting detectors, e.g. as schematically illustrated in FIG. 4. In this type of x-ray detectors, each registered photon generates a current pulse which is compared to a set of thresholds, thereby counting the number of photons incident in each of a number of so-called energy bins. This may be very useful in the image reconstruction process to increase the image quality and/or to enable a reduction of the radiation dose. Sometimes, an energy-discriminating photon-counting detector may be referred to as a multi-bin detector.

In general, the energy information allows for new kinds of images to be created, where new information is available and image artifacts inherent to conventional technology can be removed.

In other words, for an energy-discriminating detector, the pulse heights are compared to a number of programmable thresholds in the comparators and classified according to pulse-height, which in turn is proportional to energy.

However, an inherent problem in any (charge sensitive) amplifier is that it will add electronic noise to the detected current. In order to avoid detecting noise instead of real x-ray photons, it is therefore important to set the lowest threshold value high enough so that the number of times the noise value exceeds the threshold value is low enough not to disturb the detection of x-ray photons.

By setting the lowest threshold above the noise floor, electronic noise, which is the major obstacle in the reduction of radiation dose of the x-ray imaging systems, can be significantly reduced The (shaping) filter has the general property that large values of the shaping time will lead to a long pulse caused by the x-ray photon and reduce the noise amplitude after the filter. Small values of the shaping time will lead to a short pulse and a larger noise amplitude. Therefore, in order to count as many x-ray photons as possible, a large shaping time is desired to minimize noise and allowing the use of a relatively small threshold level.

Another problem in any photon-counting x-ray detector is the so-called pile-up problem. When the flux rate of x-ray photons is high there may be problems in distinguishing between two subsequent charge pulses. As mentioned above, the pulse length after the filter depends on the shaping time. If this pulse length is larger than the time between two x-ray photon induced charge pulses, the pulses will grow together and the two photons are not distinguishable and may be counted as one pulse. This is called pile-up. One way to avoid pile-up at high photon flux is to use a small shaping time.

In order to increase the absorption efficiency, the detector can be arranged edge-on, in which case the absorption depth can be chosen to any length and the detector can still be fully depleted without going to very high voltages.

Edge-on is thus a special, non-limiting design for a photon-counting detector, where the x-ray sensors such as x-ray detector elements or pixels are oriented edge-on to incoming x-rays.

For example, such an edge-on photon-counting detector may have pixels in at least two directions, wherein one of the directions of the edge-on photon-counting detector has a component in the direction of the x-rays. Such an edge-on photon-counting detector is sometimes referred to as a depth-segmented photon-counting detector, having two or more depth segments of pixels in the direction of the incoming x-rays.

Alternatively, the pixels may be arranged as an array (non-depth-segmented) in a direction substantially orthogonal to the direction of the incident x-rays, and each of the pixels may be oriented edge-on to the incident x-rays. In other words, the photon-counting detector may be non-depth-segmented, while still arranged edge-on to the incoming x-rays.

Figure 5:
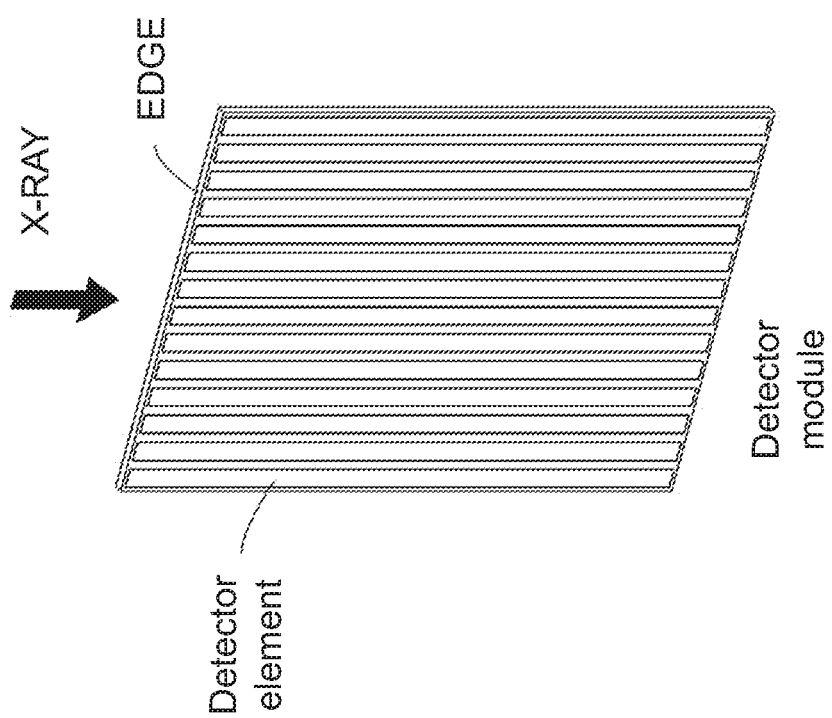
FIG. 5 is a schematic diagram illustrating an example of a semiconductor detector sub-module according to an exemplary embodiment.

FIG. 5 is a schematic diagram illustrating an example of an edge-on detector sub-module according to an exemplary embodiment. This is an example of a detector sub-module with the sensor part split into detector elements or pixels, where each detector element (or pixel) is normally based on a diode having a charge collecting electrode as a key component. The x-rays enter through the edge of the semiconductor sensor.

Figure 6:
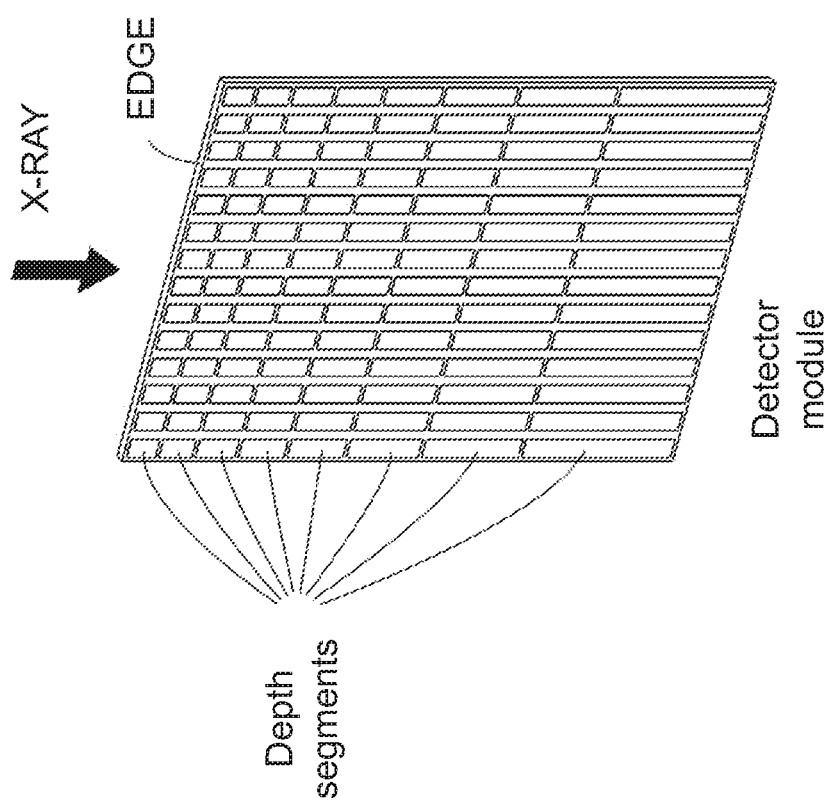
FIG. 6 is a schematic diagram illustrating an example of semiconductor detector sub-module according to another exemplary embodiment.

FIG. 6 is a schematic diagram illustrating an example of an edge-on detector sub-module according to another exemplary embodiment. In this example, the semiconductor sensor part is further split into so-called depth segments in the depth direction, again assuming the x-rays enter through the edge.

Normally, a detector element is an individual x-ray sensitive sub-element of the detector. In general, the photon interaction takes place in a detector element and the thus generated charge is collected by the corresponding electrode of the detector element.

Each detector element typically measures the incident x-ray flux as a sequence of frames. A frame is the measured data during a specified time interval, called frame time.

Depending on the detector topology, a detector element may correspond to a pixel, especially when the detector is a flat-panel detector. A depth-segmented detector may be regarded as having a number of detector strips, each strip having a number of depth segments. For such a depth-segmented detector, each depth segment may be regarded as an individual detector element, especially if each of the depth segments is associated with its own individual charge collecting electrode.

The detector strips of a depth-segmented detector normally correspond to the pixels of an ordinary flat-panel detector and are therefore sometimes also referred to as pixel strips. However, it is also possible to regard a depth-segmented detector as a three-dimensional pixel array, where each pixel (sometimes referred to as a voxel) corresponds to an individual depth segment/detector element.

The sensors may be implemented as so called Multi-Chip Modules (MCMs) in the sense that the semiconductor sensors are used as base substrates for electric routing and for a number of Application Specific Integrated Circuits (ASICs) which are attached preferably through so called flip-chip technique. The routing will include a connection for the signal from each pixel or detector element to the ASIC input as well as connections from the ASIC to external memory and/or digital data processing. Power to the ASICs may be provided through similar routing taking into account the increase in cross-section which is required for the large currents in these connections, but the power may also be provided through a separate connection.

Figure 7:
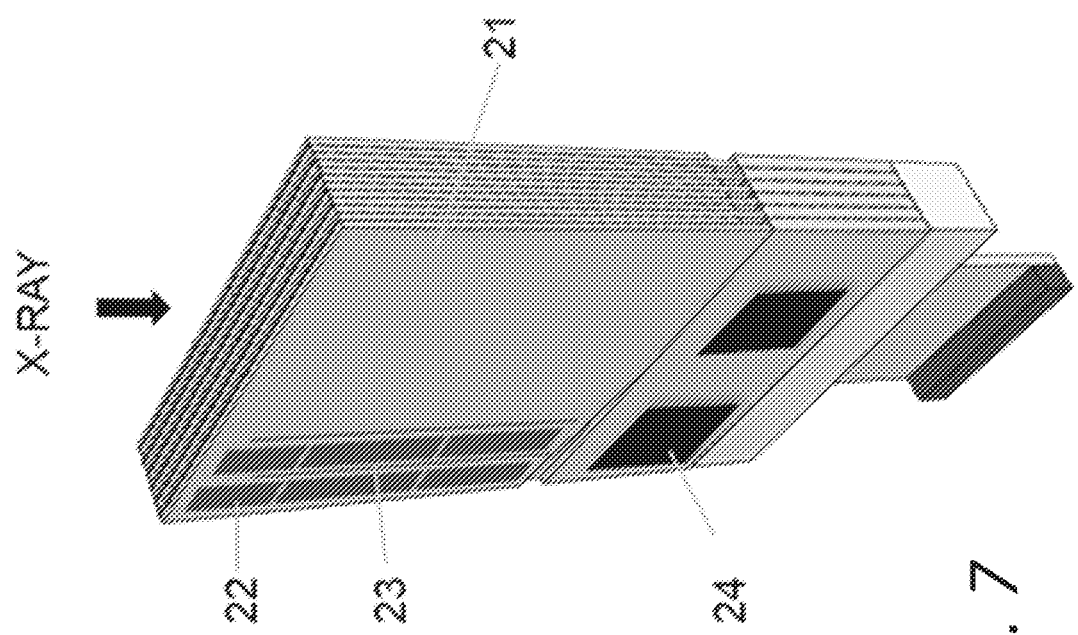
FIG. 7 is a schematic diagram illustrating an example of a set of tiled detector sub-modules, where each detector sub-module is a depth-segmented detector sub-module and the ASICs or corresponding circuitry are arranged below the detector elements as seen from the direction of the incoming x-rays.

FIG. 7 is a schematic diagram illustrating an example of a set of tiled detector sub-modules, where each detector sub-module is a depth-segmented detector sub-module and the ASICs or corresponding circuitry 24 are arranged below the detector elements 22 as seen from the direction of the incoming x-rays, allowing for routing paths from the detector elements 22 to the ASICs 23 in the space between detector elements.

As previously mentioned, pileup is a general problem related to photon-counting x-ray detectors, severely affecting the radiological images. Pileup occurs in photon-counting detectors when more than one photon hits the detector within the time window that is set by the pulse width in the electronics (the so-called dead time). Pileup leads to a loss of counts because several photons generate just a single pulse. Pileup also leads to spectral distortion because pulses within a dead time will add to a larger pulse height, which is interpreted as one photon with higher energy, and the pulses will also add to a wider pulse with a tail that may be detected as a second low-energy pulse.

Figure 8A:
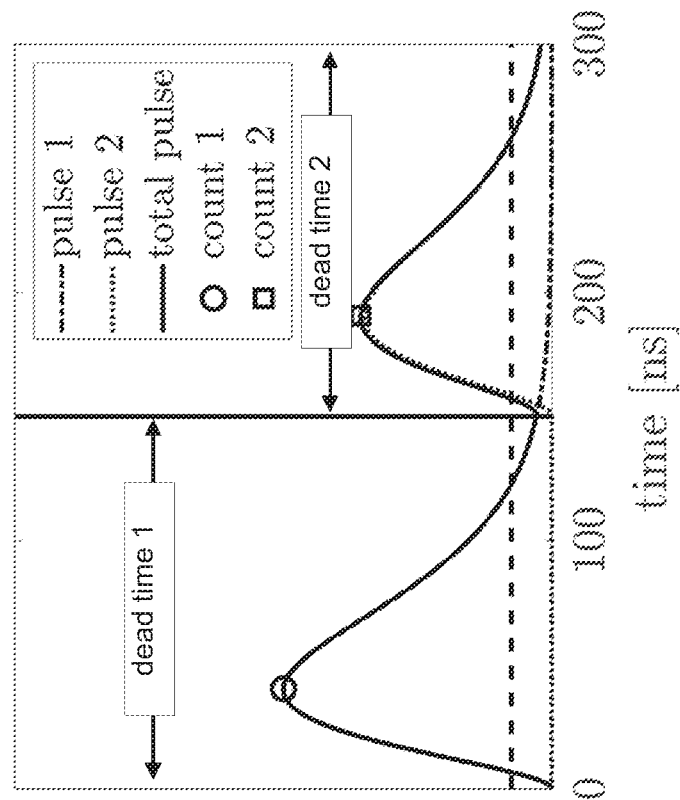
FIGS. 8A-C are schematic diagrams illustrating an example of the effect of pileup on pulse detection in a non-paralyzable photon-counting detector.
Figure 8B:
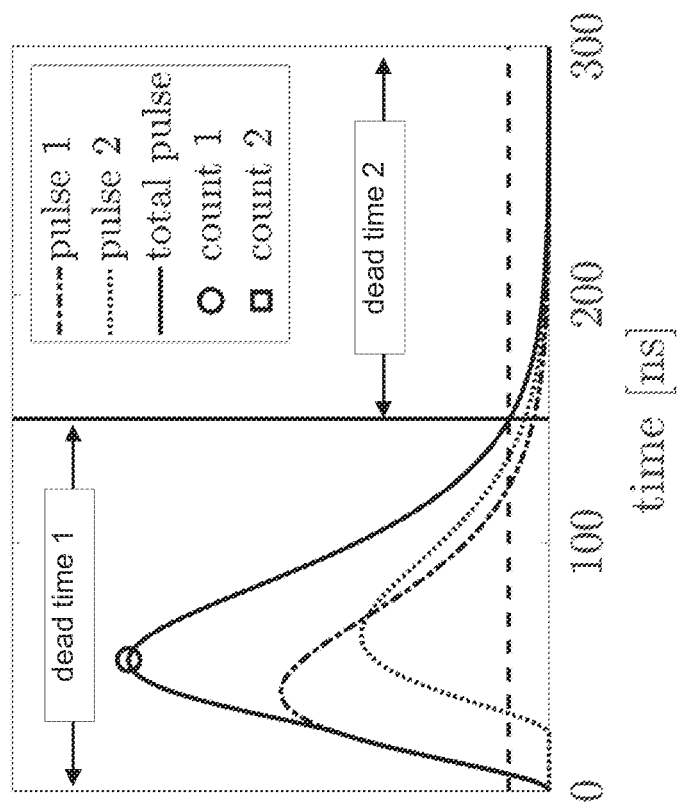
Figure 8C:
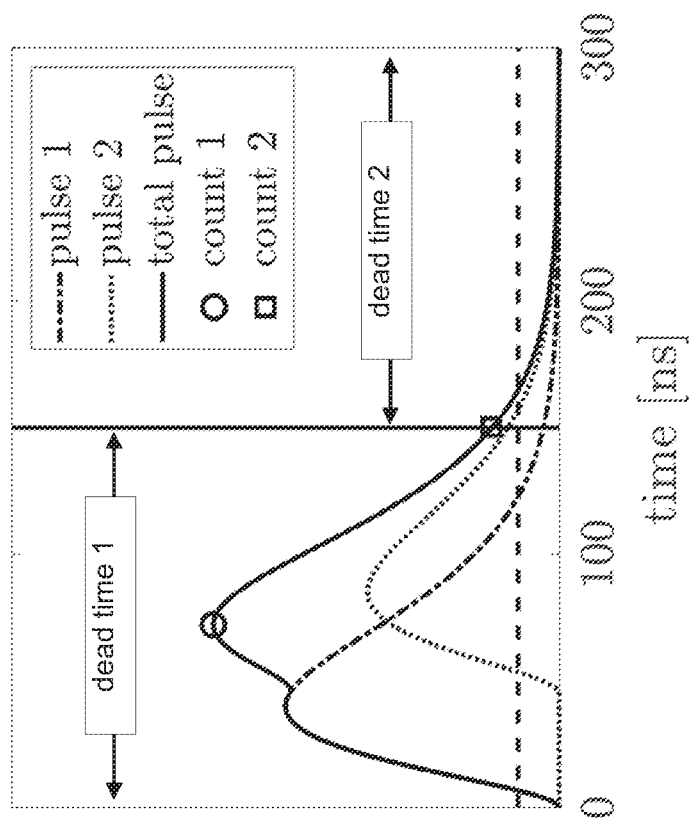

FIGS. 8A-C are schematic diagrams illustrating an example of the effect of pileup on pulse detection in a non-paralyzable photon-counting detector. When two photons interact in the detector in separate dead time windows, no pileup occurs. Two photons that interact close in time and within the same dead time window are counted as a single pulse with taller pulse height. Two photons that interact a bit further apart in time, but still within the same dead time window generate two counts, one from the overlapping taller pulse height and one from the tail of the second pulse that extends into the subsequent dead time.

Figure 9B:
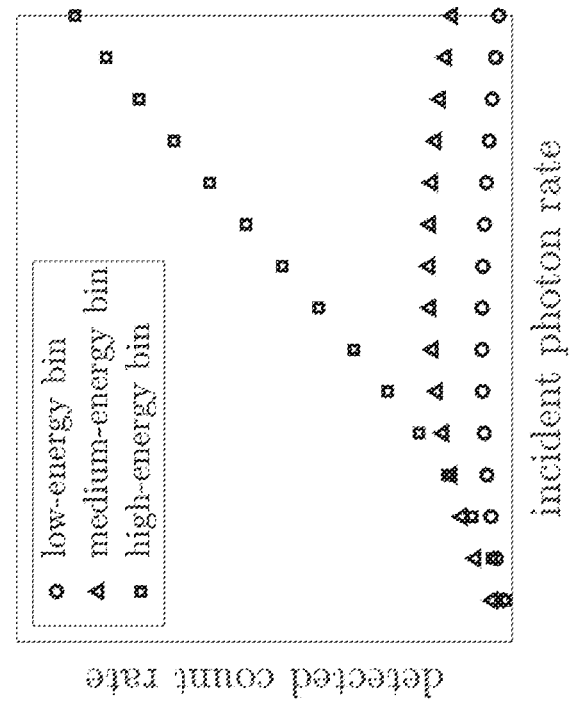
FIGS. 9A-B are schematic diagrams illustrating an example of the effect of pileup on the detection of many photons in an energy-discriminating non-paralyzable photon-counting detector.
Figure 9A:
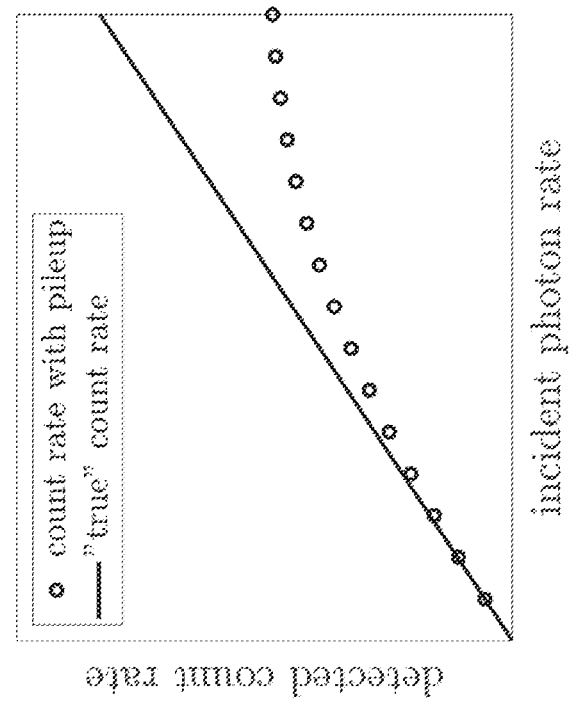

FIGS. 9A-B are schematic diagrams illustrating an example of the effect of pileup on the detection of many photons in an energy-discriminating non-paralyzable photon-counting detector. Loss of counts occurs for the sum of all energy bins, which also corresponds to the effect in a non-energy-discriminating detector. The detected count rate is a monotonically increasing function and reaches a plateau, where one count is registered per dead time window. On a bin-level, spectral distortion occurs and counts migrate between bins; detected pulse heights are pushed upwards and downwards as pulses are stacked on top of each other, and simultaneously pulse tails with lower height are detected. Generally, the former effect is stronger, and the high-energy bins tend to gain counts so that the detected count rate increases faster than linear with the incident photon rate, whereas low- and medium-energy bins lose counts so that the detected count rate reaches a maximum after which the rate declines with incident photon rate.

As discussed in the background, the methods for spectral pileup correction available in the prior art are clearly suboptimal for practical use in medical imaging systems. According to a first aspect, the proposed technology provides a method for pileup correction in a non-paralyzable energy-discriminating photon-counting x-ray detector operating based on a number of energy bins. The method basically comprises adding, for each of a number of energy bins, a correction term to the detected signal of the energy bin. The correction term is a product of two separable parameterized functions, each of which includes at least one parameter, where a first parameterized function depends on a weighted sum of the detected signal over the energy bins, and where a second parameterized function depends on the detected signal(s) in one or several energy bin(s).

The novel pile-up procedure may thus be based on providing, for each of a number of energy bins, of a detected signal, and addition of a correction term to the detected signal of the respective energy bin.

By way of example, the first parameterized function may include at least one parameter, said parameter(s) being specific to the pixel and/or depth segment and/or bin that is being corrected.

Similarly, the second parameterized function may include at least one parameter, said parameter(s) being specific to the pixel and/or depth segment and/or bin that is being corrected.

In a particular example, the x-ray detector is a depth-segmented edge-on detector and the second parameterized function further depends on the detected and/or the corrected signal(s) in one or several energy bin(s) from two or more depth segments of each detector pixel.

For example, the x-ray detector is a depth-segmented edge-on detector and the method may then further comprise an additional step of applying one or several multiplication factor(s) to the detected signal and/or the corrected count rate from two or more depth segments of each detector pixel, said multiplication factor(s) being dependent on the detected count rate and/or the corrected count rate, and said multiplication factor(s) being chosen to optimize the contrast-to-noise ratio at each count rate when the signal from said depth segments are combined to a pixel signal.

Optionally, the first function may for example be a rational function. Alternatively, the first function may for example be an exponential function.

Optionally, the second function may be a linear combination of the signal from all bins, i.e. a matrix operator with a size corresponding to the number of bins squared.

In a particular example, the method further comprises the step of performing calibration of at least a subset of the parameter(s) of the first parameterized function and/or the second parameterized function and/or the parameters of the weighted sum.

By way of example, at least a subset of the parameters of the first parameterized function and/or the second parameterized function and/or the parameters of the weighted sum may be determined and/or calibrated by exposing the x-ray detector with a range of photon rates, resulting in different levels of pileup.

For example, the range of photon rates may be generated by varying the x-ray tube current.

Alternatively, the range of photon rates may be generated by a range of material combinations in the beam path.

As an example, the expected count rate free from pileup at any count rate may be determined by extrapolation from low count rates, and the parameters may be determined by inverting the product of the two separable parameterized functions, analytically and/or iteratively.

In another example, the expected count rate free from pileup at any count rate may be determined by the statistics over two or more realizations at each average photon rate, and the parameters may be determined by inverting the product of the two separable parameterized functions, analytically and/or iteratively.

In other words, the proposed technology relates to a procedure for correction of the pileup effect based on adding a correction term separately on each considered energy bin.

For a better understanding, the proposed technology will now be described with reference to non-limiting examples.

A main advantage of the proposed invention over the prior art is the ability to correct for spectral pileup at a low level of algorithmic and/or computational complexity, e.g. in terms of the number of parameters and computational burden.

By way of example, this advantage may be enabled by splitting the procedure/algorithm into two separable functions, where the first function depends on a weighted or unweighted sum of the detected signal over the energy bins, i.e. essentially the non-spectral signal, and the second part depends on the distribution of signal in the energy bins, i.e. essentially the spectral response normalized by the non-spectral signal.

For example, consider an energy-discriminating photon-counting detector with a detected signal $S_i$ in energy bin i out of N total energy bins. The detected signal $S_i$ is closely related to the number of detected x-ray photons in the energy interval $E_i \leq E < E_{i+1}$, where $E_i$ and $E_{i+1}$ are the lower and upper threshold energies that define the energy bin. It is then possible to define a pile-up corrected signal as:

$$\hat{S}_i = S_i + \alpha(S_w, a_i) \cdot \beta(S, S_w, b_i), \text{ where } S_w = A \cdot S. \tag{1}$$

The N-by-1 vector S is the bin response, i.e. the detected signal per energy bin, and A is a 1-by-N vector of parameters. The dot product $A \cdot S$ yields a scalar $S_w$, which is an invertible (one-to-one) function of the input count rate. The function $\alpha$ has a set of K parameters, $a_i = [a_{i,1} \ldots a_{i,K}]$ and the function $\beta$ has a set of L parameters $b_i = [b_{i,1} \ldots b_{i,L}]$. The function parameter sets $a_i$ and $b_i$ may depend on the energy bin index i, but the functions $\alpha$ and $\beta$ are otherwise identical across all N energy bins and both yield a scalar per energy bin.

The principle behind Eq. (1) is that $\alpha(S_w)$ corrects for mean behavior, whereas $\beta(S, S_w)$ corrects for variations around the mean. By assuming that these two phenomena are separable, any cross correlations are ignored, which reduces the number of parameters and the complexity of the pileup correction algorithm substantially. The low complexity strongly facilitates firmware implementation, which enables data reduction at an early stage in the image chain, thereby improving speed and data handling performance of the x-ray imaging system.

One conceivable scenario is that the function $\alpha$ compensates for the loss of counts per bin as the non-spectral signal $S_w$ for some A is an injective (one-to-one) function of the true count rate. In the same scenario, the function $\beta$ instead handles correlation, i.e. the migration of counts between energy bins, which is virtually independent of the count rate.

If the detector pixels are equipped with depth segments, some segments may see a relatively lower count rate because of absorption in the top layers and/or because of the choice of absorption length of the layers. The spectrum detected in the depth segments with lower count rate is generally closer to the "true" spectrum, i.e. the spectrum that would have been detected without pileup. This fact can be utilized by the function β to correct for the migration of counts between energy bins if Eq. (1) is generalized to the signal in bin i and segment j of a detector with a total of N energy bins and M depth segments:

$$\hat{S}_{i,j}=S_{i,j}+\alpha_j(S_{j_w},\alpha_{j_i})\cdot\beta_j(S,S_{j_w},b_{j_i}), \text{ where } S_{j_w}=A_j\cdot S_j. \quad (2)$$

In Eq. (2), the N-by-M matrix S is the segment dependent bin response, i.e. the detected signal per energy bin and depth segment, $S_j$ is the bin response for segment j, and $A_j$ is a 1-by-N vector of parameters for segment j. The functions $\alpha_j$ and $\beta_j$ as well as the function parameter sets $a_{j_i}$ and $b_{j_i}$ may depend on the depth segment. The functions $\alpha_j$ and $\beta_j$ may, however, be constant for a certain depth segment j, whereas the parameter sets $\alpha_{j_i}$ and $b_{j_i}$ may depend on the energy bin index i.

Another way of utilizing a difference in count rate between depth segments is weighting of the layers according to count rate, which may be optimal from the perspective of contrast-to-noise ratio, i.e. the low-count layers will be assigned relatively higher weights at higher count rates. The pileup correction algorithm defined by Eq. (1) and Eq. (2) generalizes to segment weighting; either S in Eq. (1) is already a segment weighted bin response $S=\Sigma_{j=1}^{M} w_j S_j$, or S is a function of segment and weighting is applied on the corrected bin response $\hat{S}$ post pileup correction, i.e. $\hat{S}=\Sigma_{j=1}^{M} w_j \hat{S}_j$.

Figure 10:
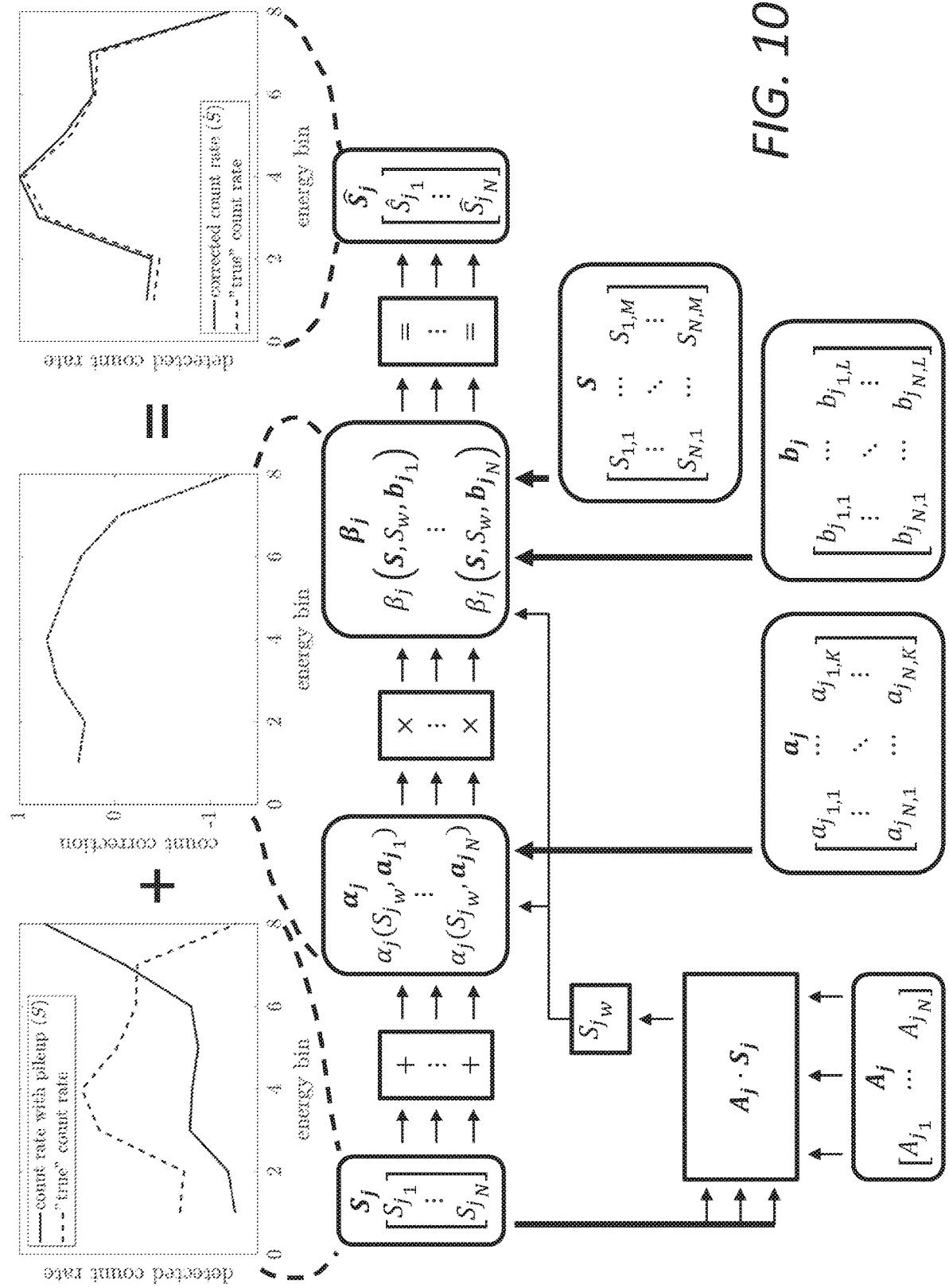
FIG. 10 is a schematic flow chart illustrating a particular, non-limiting example of a method for pileup correction of N energy bins.
Figure 11:
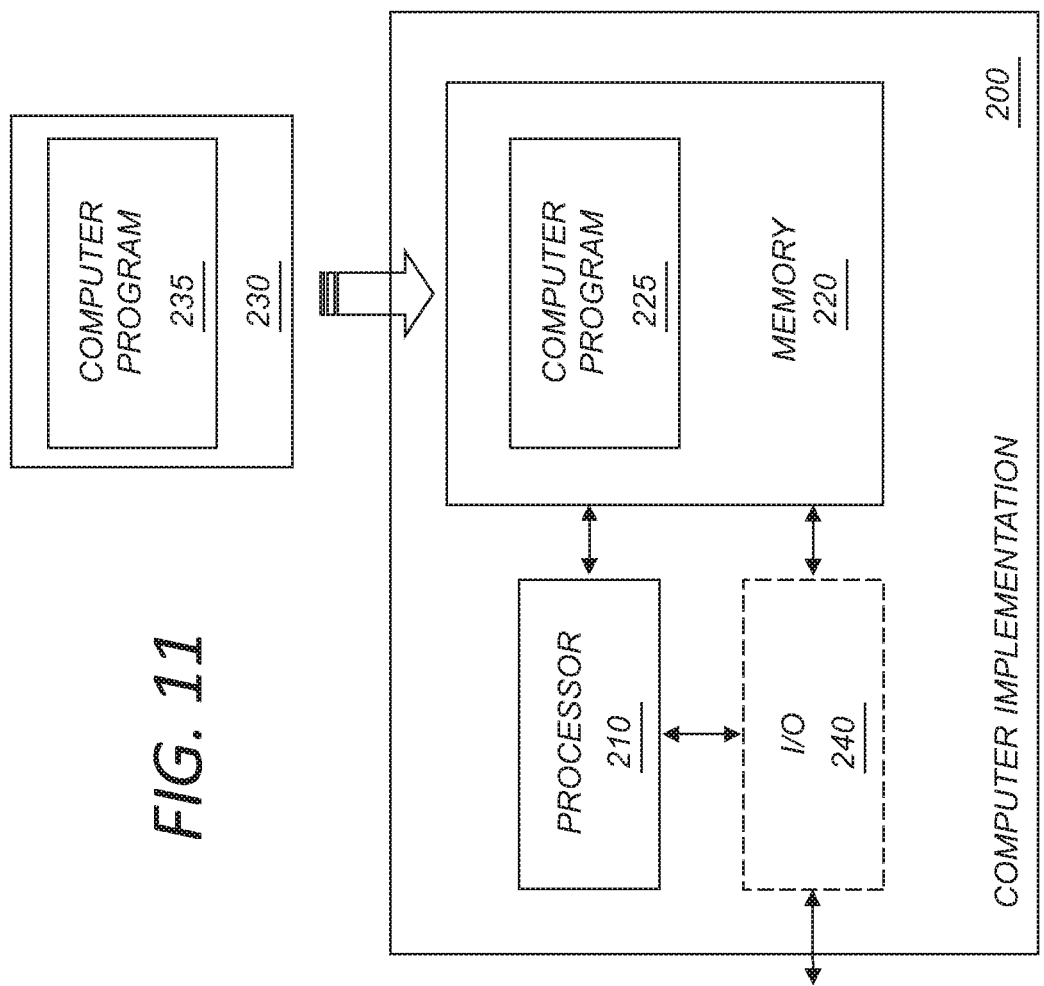
FIG. 11 is a schematic diagram illustrating an example of a computer implementation according to an embodiment.

FIG. 10 is a schematic flow chart illustrating a particular, non-limiting example of a method for pileup correction of N energy bins in depth segment j in a detector with a total of M depth segments. Thin arrows illustrate transfer of scalars between the various steps, whereas thick lines illustrate vectors, i.e., a multitude of scalars. In the same manner, bold symbols refer to vectors, whereas non-bold symbols refer to scalars. Each step of the method is illustrated by a plot for the example of N=8 energy bins and a typical pileup level: The detected signal ($S_j$) is illustrated and compared to the "true" signal per energy bin, i.e. the signal that would have been detected without pileup; the additive count correction, i.e. the product of the functions α and β, is illustrated as a factor that varies between positive and negative values because counts are added and subtracted depending on energy bin; the corrected signal per energy bin ($\hat{S}_j$) is illustrated and compared to the "true" signal per energy bin. In this exemplary case, the correspondence between the corrected signal and the "true" signal is excellent.

The parameter sets a and b inherent to the functions α and β may vary with energy bin because different energy bins have different response to the pileup effect. In particular, pileup tends to push detected pulse heights upwards and downwards as pulses are stacked on top of each other, and simultaneously pulse tails with lower height are detected. Generally, the former effect is stronger, and the high-energy bins tend to collect more counts on expense of the low-energy bins as pileup progresses. Further, the parameter sets a and b, as well as the parameters in the vector A, may vary with pixel and/or depth segment because of non-uniformities in the detector.

The parameter sets a and b inherent to the functions α and β and the vector A may, fully or partly, be determined theoretically, based on known properties of the detector. Nevertheless, it is likely that at least a subset of the parameters is preferentially determined by a calibration procedure. A calibration procedure can, for instance, be set up such that the detector is exposed to a range of x-ray photon rates that result in a range of count rates in the detector. The range of photon rates can be generated by operating the x-ray tube at various tube currents and/or by introducing filtering materials in the beam with various thicknesses. In this scenario, the "true" signal per energy bin, i.e. the signal that would have been detected without pileup, can be inferred by extrapolating the signal detected at low count rates, assuming linearity with tube current and/or any other known function of tube current and material thickness. Another option to determine the "true" count rate is to measure the statistics, for instance the variance, over several realizations at each average photon rate and using a known function for how the statistics vary with the loss of counts to pileup, such as the relationship described in Ref. 2. Once the "true" count rate is known, the set of parameters can be determined by inverting Eq. (1) and/or Eq. (2), either analytically or iteratively using any well-known optimization method.

The corrected detector response $\hat{S}$ may continue to propagate through the imaging chain to a final image. For the energy-discriminating photon-counting detector, a major step of the imaging chain may be material decomposition, which transfers the detector signal to two or more material bases.[7] The material bases may be combined to highlight a certain material in the body or to maximize the overall contrast-to-noise ratio. For a CT system, another major step of the imaging chain is reconstruction of the image from projections at a range of view angles using a method such as filtered back projection or iterative reconstruction.

It will be appreciated that the methods and devices described herein can be combined and re-arranged in a variety of ways.

For example, specific functions may be implemented in hardware, or in software for execution by suitable processing circuitry, or a combination thereof.

The steps, functions, procedures, modules and/or blocks described herein may be implemented in hardware using any conventional technology, such as semiconductor technology, discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs).

Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

By way of example, it is possible to implement the pileup correction procedure/algorithm on an FPGA.

It should also be understood that it may be possible to re-use the general processing capabilities of any conventional device or unit in which the proposed technology is implemented. It may also be possible to re-use existing software, e.g. by reprogramming of the existing software or by adding new software components.

According to a particular aspect, there is provided a system for pileup correction in a non-paralyzable energy-discriminating photon-counting x-ray detector operating based on a number of energy bins. The system is configured to add, for each of a number of energy bins, a correction term to the detected signal of the energy bin, said term being a product of two separable parameterized functions, each of which includes at least one parameter, where a first parameterized function depends on a sum of the detected signal over the energy bins, and where a second parameterized function depends on the detected signal(s) in one or several energy bin(s).

By way of example, the system may be implemented in hardware and/or firmware.

For example, the system may be implemented based on Field Programmable Gate Array (FPGA) technology.

According to another aspect, as mentioned, there is provided a system for x-ray imaging comprising a system for pileup correction as described herein.

By way of example, the x-ray imaging system may be configured for computed tomography.

As another example, the x-ray imaging system may be configured for mammography.

FIG. 19 is a schematic diagram illustrating an example of a computer implementation according to an embodiment. In this particular example, the system 200 comprises a processor 210 and a memory 220, the memory comprising instructions executable by the processor, whereby the processor is operative to perform the steps and/or actions described herein. The instructions are typically organized as a computer program 225; 235, which may be preconfigured in the memory 220 or downloaded from an external memory device 230. Optionally, the system 200 comprises an input/output interface 240 that may be interconnected to the processor(s) 210 and/or the memory 220 to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

In particular, the proposed technology also provides a computer-program comprising instructions, which when executed by a processor, cause the processor to perform the method for pileup correction as described herein.

The proposed technology also provides a computer-program product comprising a non-transitory computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

Method flows may be regarded as a computer action flows, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively, it is possibly to realize the modules predominantly by hardware modules, or alternatively by hardware. The extent of software versus hardware is purely implementation selection.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

REFERENCES

1. Knoll G F. *Radiation Detection and Measurement.* 3rd ed. John Wiley & Sons; 2000.
2. Grönberg F, Danielsson M, Sjölin M. Count statistics of nonparalyzable photon-counting detectors with nonzero pulse length. *Med Phys.* 2018; 45(8):3800-3811.
3. Sabbatucci L, Fernández J E. First principles pulse pile-up balance equation and fast deterministic solution. *Radiat Phys Chem.* 2017; 137:12-17.
4. Cammin J, Kappler S, Weidinger T, Taguchi K. Evaluation of models of spectral distortions in photon-counting detectors. *J Med Imaging.* 2016; 3(2).
5. Feng R, Rundle D, Wang G. Neural-networks-based Photon-Counting Data Correction: Pulse Pileup Effect. In: *IEEE.* 2018:1-14.
6. Alvarez R E. Near optimal neural network estimator for spectral x-ray photon counting data with pileup. *ArXiv.* 2017:1-11.
7. Alvarez R E, Macovski A. Energy-selective reconstructions in X-ray computerized tomography. *Phys Med Biol.* 1976; 21(5):733-744.

The invention claimed is:

1. A method for pulse pileup correction in a non-paralyzable energy-discriminating photon-counting x-ray detector operating based on a number of energy bins, the method comprising:

the non-paralyzable energy-discriminating photon-counting x-ray detector registering radiation from an x-ray source and generating a detected signal, each said detected signal being assigned to a respective one of a number of energy bins;

the non-paralyzable energy-discriminating photon-counting x-ray detector adding, for each respective one of the energy bins, a signal correction term to the detected signal of the energy bin, said signal correction term being a product of two separable parameterized functions, each of said two separable parameterized functions including at least one parameter, where a first of said two separable parameterized functions depends on a weighted sum of the detected signal over the energy bins, and where a second of said two separable parameterized functions depends on the detected signal(s) in at least one of the energy bins; and the non-paralyzable energy-discriminating photon-counting x-ray detector generating image data using the detected signal(s) of the energy bins with the respective signal correction term having been added, the generated radiological image data being provided for image generation.

2. The method according to claim 1, in which said first parameterized function includes at least one parameter, said parameter(s) being specific to the pixel and/or depth segment and/or bin that is being corrected.

3. The method according to claim 1, in which said second parameterized function includes at least one parameter, said parameter(s) being specific to the pixel and/or depth segment and/or bin that is being corrected.

4. The method according to claim 1, wherein the x-ray detector is a depth-segmented edge-on detector and in which said second parameterized function further depends on the detected and/or the corrected signal(s) in one or several energy bin(s) from two or more depth segments of each detector pixel.

5. The method according to claim 1, wherein the x-ray detector is a depth-segmented edge-on detector and the method further comprises an additional step of applying one or several multiplication factor(s) to the detected signal and/or the corrected count rate from two or more depth segments of each detector pixel, said multiplication factor(s) being dependent on the detected count rate and/or the corrected count rate, and said multiplication factor(s) being chosen to optimize the contrast-to-noise ratio at each count rate when the signal from said depth segments are combined to a pixel signal.

6. The method according to claim 1, in which said first function is a rational function.

7. The method according to claim 1, in which said first function is an exponential function.

8. The method according to claim 1, in which said second function is a linear combination of the signal from all bins, i.e. a matrix operator with a size corresponding to the number of bins squared.

9. The method according to claim 1, further comprising the step of performing calibration of at least a subset of the parameter(s) of the first parameterized function and/or the second parameterized function and/or the parameters of the weighted sum.

10. The method according to claim 9, in which at least a subset of the parameters of the first parameterized function and/or the second parameterized function and/or the parameters of the weighted sum are determined and/or calibrated by exposing the x-ray detector with a range of photon rates, resulting indifferent levels of pileup.

11. The method according to claim 10, in which the range of photon rates is generated by varying the x-ray tube current.

12. The method according to claim 10, in which the range of photon rates is generated by a range of material combinations in the beam path.

13. The method according to claim 10, in which the expected count rate free from pileup at any count rate is determined by extrapolation from low count rates, and the parameters are determined by inverting the product of the two separable parameterized functions, analytically and/or iteratively.

14. The method according to claim 10, in which the expected count rate free from pileup at any count rate is determined by the statistics over two or more realizations at each average photon rate, and the parameters are determined by inverting the product of the two separable parameterized functions, analytically and/or iteratively.

15. A non-transitory computer-readable medium on which is stored a computer program comprising instructions, which when executed by a processor, cause the processor to perform the method of claim 1.

16. A system for pulse pileup correction in a non-paralyzable energy-discriminating photon-counting x-ray detector operating based on a number of energy bins, the system comprising:

processing circuitry configured to perform signal processing by adding, for each of a number of energy bins, a signal correction term to a detected signal of each of the energy bins, said signal correction term being a product of two separable parameterized functions, each of said two separable parameterized functions including at least one parameter, where a first of said two separable parameterized functions depends on a sum of the detected signal over the energy bins, and where a second of said two separable parameterized functions depends on the detected signal(s) in at least one of the energy bins, the processing circuitry generating image data using the detected signal(s) of the energy bins with the signal correction term having been added, the generated radiological image data being provided for image generation.

17. The system according to claim 16, wherein the system is implemented in hardware and/or firmware.

18. The system according to claim 16, wherein the system is implemented based on Field Programmable Gate Array (FPGA) technology.

19. A system for x-ray imaging comprising a system for pileup correction according to claim 16.

20. The x-ray imaging system according to claim 19, wherein the x-ray imaging system is configured for computed tomography.

21. The x-ray imaging system according to claim 19, wherein the x-ray imaging system is configured for mammography.

* * * * *